(12) United States Patent
Snowball (10) Patent No.: US 10,178,874 B2
(45) Date of Patent: Jan. 15, 2019

(54) STERILISATION OF PACKAGE ARTICLES

(71) Applicant: Ozonica Limited, Northhamptonshire (GB)

(72) Inventor: Malcolm Robert Snowball, Epping (GB)

(73) Assignee: Ozonica Limited, Northhamptonshire (GB)

( * ) Notice: Subject to any disclaimer, the term of this patent is extended or adjusted under 35 U.S.C. 154(b) by 0 days.

(21) Appl. No.: 15/181,258

(22) Filed: Jun. 13, 2016

(65) Prior Publication Data

US 2016/0286846 A1     Oct. 6, 2016

Related U.S. Application Data

(63) Continuation of application No. 13/263,338, filed as application No. PCT/GB2010/050606 on Apr. 7, 2010, now abandoned.

(30) Foreign Application Priority Data

Apr. 7, 2009   (GB) .................................. 0906091.4
May 27, 2009   (GB) .................................. 090111.7

(51) Int. Cl.
*A23L 3/3445*     (2006.01)
*A61L 2/14*     (2006.01)
(Continued)

(52) U.S. Cl.
CPC ............... *A23L 3/3445* (2013.01); *A23L 3/26* (2013.01); *A23L 3/34095* (2013.01); *A61L 2/14* (2013.01);
(Continued)

(58) Field of Classification Search
CPC ...... A23L 3/3445; A23L 3/26; A23L 3/34095; B65B 55/08; B65B 55/16; B65B 55/02; A61L 2/14
See application file for complete search history.

(56) References Cited

U.S. PATENT DOCUMENTS 1,888,421 A    11/1932   Beck
3,600,126 A     8/1971   Hellund
(Continued)

FOREIGN PATENT DOCUMENTS

CN        2155368 Y    2/1994
DE    196 40 528 A1    4/1998
(Continued)

OTHER PUBLICATIONS

English translation of JP2004209188, Jul. 29, 2004.*
(Continued)

*Primary Examiner* — Regina M Yoo
(74) *Attorney, Agent, or Firm* — Hickman Palermo Becker Bingham LLP; Malgorzata A. Kulczycka (57) ABSTRACT

An apparatus for sterilising a packaged product (16) such as food or drink comprises a pair of gas filled electrodes (1, 2) connected to a power supply (18) for generating a high voltage pulses between the electrodes (1, 2) sufficient to ionise the gas therein and to create a high electromagnetic field therebetween. A reflector (7) is provided for directing the generated field towards the package (16), such that the electromagnetic field penetrates through the wall of the package (16) and forms cold plasma from the trapped air inside the package (16). This cold plasma comprises ozone and other reactive oxygen based species which have a high oxidizing potential and kill all microorganisms in contact (Continued)

with the ozone and reactive species resulting in the disinfection of the product as well as the interior of the sealed package.

13 Claims, 5 Drawing Sheets

(51) Int. Cl.

| | | |
|---|---|---|
| *B65B 55/02* | (2006.01) | |
| *A23L 3/3409* | (2006.01) | |
| *A23L 3/26* | (2006.01) | |
| *B65B 55/08* | (2006.01) | |
| *B65B 55/16* | (2006.01) | |
| *A61L 2/20* | (2006.01) | |

(52) U.S. Cl.
CPC .............. *B65B 55/02* (2013.01); *B65B 55/08* (2013.01); *B65B 55/16* (2013.01); *A23V 2002/00* (2013.01); *A61L 2/202* (2013.01)

(56) References Cited

U.S. PATENT DOCUMENTS

| | | | | |
|---|---|---|---|---|
| 3,798,922 | A * | 3/1974 | Duke ................. | F24F 3/166 422/186.07 |
| 3,971,968 | A | 7/1976 | Bachmann et al. | |
| 4,042,325 | A * | 8/1977 | Tensmeyer ............... | A61L 2/14 219/121.84 |
| 4,167,669 | A | 9/1979 | Panico | |
| 4,374,406 | A | 2/1983 | Hepp | |
| 4,417,172 | A | 11/1983 | Touhou et al. | |
| 5,004,587 | A * | 4/1991 | Tacchi .................... | C01B 13/11 422/186.07 |
| 5,411,713 | A * | 5/1995 | Iwanaga ................. | C01B 13/11 204/176 |
| 5,451,368 | A | 9/1995 | Jacob | |
| 6,007,770 | A * | 12/1999 | Peiper ...................... | A61L 2/202 422/22 |
| 6,187,001 | B1 | 2/2001 | Azar et al. | |
| 6,998,580 | B2 | 2/2006 | Kusuda et al. | |
| 7,126,091 | B1 | 10/2006 | Westfall | |
| 7,178,744 | B2 | 2/2007 | Tapphorn | |
| 8,135,051 | B2 | 3/2012 | Sato et al. | |
| 2001/0005116 | A1 | 6/2001 | Takahashi et al. | |
| 2002/0168466 | A1 | 11/2002 | Tapphorn | |
| 2003/0152480 | A1 * | 8/2003 | Sham ..................... | A61L 2/26 422/28 |
| 2003/0183168 | A1 | 10/2003 | Kusuda et al. | |
| 2004/0037736 | A1 * | 2/2004 | Perruchot ................ | A61L 2/24 422/22 |
| 2005/0133740 | A1 | 6/2005 | Gardner | |
| 2005/0153069 | A1 | 7/2005 | Tapphorn | |
| 2006/0042545 | A1 | 3/2006 | Shibata et al. | |
| 2006/0127271 | A1 | 6/2006 | Raun | |
| 2006/0268192 | A1 | 11/2006 | Nishiyama et al. | |
| 2007/0066971 | A1 | 3/2007 | Podhajsky | |
| 2008/0055594 | A1 | 3/2008 | Hadidi | |
| 2008/0145553 | A1 | 6/2008 | Boulos | |
| 2008/0314251 | A1 * | 12/2008 | Tanaka .................. | B01D 53/32 96/95 |
| 2009/0057131 | A1 | 3/2009 | Tarnovsky | |
| 2009/0244396 | A1 | 10/2009 | Takata | |
| 2010/0223944 | A1 * | 9/2010 | Tsujimoto ............ | A23B 7/0433 62/264 |
| 2010/0236269 | A1 * | 9/2010 | Mamemoto .......... | A23B 7/0425 62/331 |
| 2010/0308730 | A1 | 12/2010 | Mohamed | |
| 2011/0022043 | A1 | 1/2011 | Wandke | |
| 2012/0213664 | A1 | 8/2012 | Diver et al. | |
| 2012/0314333 | A1 * | 12/2012 | Takeda ..................... | A61L 9/22 361/230 |

FOREIGN PATENT DOCUMENTS

| | | |
|---|---|---|
| DE | 198 14865 A1 | 10/1999 |
| EP | 0948969 A1 | 10/1999 |
| EP | 1 726 314 A1 | 11/2006 |
| JP | 201145689 A | 5/2001 |
| JP | 2004026171 A | 1/2004 |
| JP | 2004209188 | 7/2004 |
| RU | 2050653 C1 | 12/1995 |
| RU | 2086262 C1 | 8/1997 |
| RU | 2003127157 A | 3/2005 |
| WO | WO02/071438 A2 | 9/2002 |
| WO | WO2009/003613 A1 | 1/2009 |
| WO | WO 2009/040130 A | 4/2009 |
| WO | WO2010/116191 A1 | 10/2010 |
| WO | WO 2011/055113 A | 5/2011 |
| WO | WO2011116984 | 9/2011 |
| WO | WO 2011/137359 | 11/2011 |

OTHER PUBLICATIONS

International Search Report in application No. PCT/GB2012/051017 dated Apr. 2, 2013, 5 pages.
Intellectual Property Office, "Search Report" in application No. GB1208102.2 dated Sep. 5, 2012, 2 pages.
Intellectual Property Office, "Search Report" in application No. GB1205611.5 dated Jul. 20, 2012, 6 pages.
European Patent Office, "Search Report" in application No. 10 714 670.6-1356, dated Jun. 26, 2015, 5 pages.
Claims in European Application No. 10 714 670.6-1356, dated Jun. 2015, 3 pages.
U.S. Appl. No. 13/263,338, filed Dec. 29, 2011, Office Action, dated Jul. 21, 2014.
U.S. Appl. No. 13/263,338, filed Dec. 29, 2011, Office Action, dated Oct. 6, 2014.
U.S. Appl. No. 13/263,338, filed Dec. 29, 2011, Office Action, dated Jan. 11, 2016.
U.S. Appl. No. 13/263,338, filed Dec. 29, 2011, Notice of Allowability, dated Aug. 13, 2015.
U.S. Appl. No. 13/263,338, filed Dec. 29, 2011, Interview Summary, dated May 31, 2016.
U.S. Appl. No. 13/263,338, filed Dec. 29, 2011, Final Office Action, dated Apr. 13, 2015.
U.S. Appl. No. 13/263,338, filed Dec. 29, 2011, Notice of Allowance, dated Jul. 30, 2015.

* cited by examiner

STERILISATION OF PACKAGE ARTICLES

CROSS-REFERENCE TO RELATED APPLICATIONS; BENEFIT CLAIM

This application claims the benefit as a Continuation of application Ser. No. 13/263,338, filed Dec. 29, 2011 which claims priority to foreign application no. PCT/GB2010/050606, filed Apr. 7, 2010, which claims priority to GB application No. 0906091.4, filed Apr. 7, 2009, which claims priority to GB application No. 090111.7, filed May 27, 2009, the entire contents of which is hereby incorporated by reference as if fully set forth herein, under 35 U.S.C. § 120. The applicant(s) hereby rescind any disclaimer of claim scope in the parent application(s) or the prosecution history thereof and advise the USPTO that the claims in this application may be broader than any claim in the parent application(s).

This invention relates a method an apparatus for the sterilisation or disinfection of packaged articles such as packaged food and drink products.

The shelf life of food is substantially shortened due to the presence of micro-organisms in the food, which can cause the food to deteriorate. Not only does shelf life affect the economic viability of food producers but it has a direct effect on public health, since the presence of certain micro-organisms in food can be hazardous if the food is ingested. These problems can be exacerbated if the food is not kept sufficiently refrigerated, since the micro-organisms in the food can multiply rapidly.

In order to overcome the above-mentioned problems, it has been proposed to pasteurise food. However, a disadvantage of pasteurisation is that the process is lengthy and can only be used on certain types of food. Furthermore, the pasteurisation process affects the taste of the food and is costly to perform, since it uses a substantial amount of energy, a great deal of which is discharged into the working environment.

In one known method, the food is packaged in an atmosphere which inhibits the fast reproduction of micro organisms. One such an approach is to package the food product within a carbon dioxide atmosphere. This has proved to be difficult to control, environmentally unfriendly and expensive to run.

GB2457057 discloses an alternative method in which the food product is disinfected by irradiating it with UV light through its sealed packaging. This method requires the packaging material to pass the disinfection wavelengths (around 260 nm) at high efficiencies, otherwise high power is required to get sufficient UV intensity into the package to disinfect the food. Present packaging materials are poor transmitters of these UV wavelengths and therefore special packaging materials need to be used. Such packaging materials are expensive and necessitate modifications to the existing packaging processes, which mean that the whole food industry will have to change its packaging equipment or develop a whole new family of packaging materials.

In order to achieve adequate disinfection inside a sealed package it is necessary that all of the product surfaces are irradiated with the UV light. This is extremely difficult to achieve, for example in the case of sliced meat or cheese where the light will not reach between the slices therefore the disinfection effect will be marginal and therefore the shelf life will not be improved. The method also suffers from a susceptibility to dust and dirt, since the UV lamps must be clean at all times and it will be appreciated that the general environment in the food processing industry does not lend itself to this.

This method also has the added disadvantage that the UV light must have a clear "window" to penetrate the package i.e. no labelling or printing on the package. This makes the packaging process inflexible and forces packaging process redesign.

It is well known that ozone is a highly oxidising gas, which is a very efficient disinfector of micro-organisms. Ozone has a very short life (about 20 minutes) before it naturally reverts back to oxygen and therefore ideally suited for extending the shelf life of food sold in sealed packages and for killing other harmful micro-organisms that may be contained in the food such as e-coli.

GB2457057 also discloses a method in which the food product is further disinfected in its sealed package by creating ozone inside the package using UV light of ozone producing wavelengths. Ozone, being a gas with very efficient disinfection properties, will permeate everywhere inside the sealed package and will therefore disinfect the product. Unfortunately this method suffers from the same disadvantages as the above-mentioned UV disinfection method, in that the packaging materials to pass such UV wavelengths are even more special and are expensive to buy and process. Also, the ozone producing wavelengths are in the vacuum UV range (around 185 nm) and known packaging materials pass these wavelengths inefficiently and hence are energy inefficient.

In practice, the amount of ozone produced by UV methods is relatively low and is significantly affected by atmospheric humidity. Accordingly, in a fixed flow process where the time to dose each package is fixed, it is very difficult to get a consistent ozone dose. This method also produces nitrous oxide as a by product from the air inside the package which is undesirable, since nitrous oxide combined with water produces nitric acid which will damage the product. Another drawback to this approach is that there is an amount of unwanted ozone produced in the air spaces surrounding the UV lamp, which must be neutralized as free ozone is a regulated substance because the presence of ozone in the atmosphere presents a health hazard.

This method also has the added disadvantage that the UV must have a clear window to penetrate the package i.e. no labelling or printing on the package. This makes the packaging process inflexible and forces packaging process redesign.

Another known method of sterilising food comprises creating ozone inside a sealed package using a conventional corona discharge methods. This entails a metal electrode placed either side of the sealed package and a high voltage ac supply connected to the electrodes. The high voltage creates a corona discharge between the electrodes, which then converts some of the oxygen in the air in the package to ozone.

Whilst this method avoids some of the problems with the UV irradiation method, it still suffers from some serious shortcomings. The method uses metal electrodes, which heat up to a significantly high temperature during operation and therefore need to be force cooled. These electrodes are in close proximity to the packaging material and hence have to be cooled to less than 70° C., otherwise the packaging material is degraded. This usually requires water cooling with its associated pumping and heat exchanger systems. This method is a discharge system, which means that electrons are discharged between the electrodes under high voltage conditions: as a consequence there is erosion and hence deterioration of the electrodes leading to short electrode life and hence poor reliability. Discharges of this technology are uncontrolled avalanche types, which not only penetrate the packaging material but also the product and can be very detrimental to some products. This method usually cannot be repeated more than once as the product deterioration due to repeated corona discharge is unacceptable. Corona discharge whilst producing medium to high levels of ozone also suffers from inconsistent ozone production due to atmospheric humidity and worse produces high levels of nitrous oxide from the nitrogen in the air inside the package. As a consequence this method is usually confined to applications where the packaging environment is pure oxygen and hence no nitrous oxide is formed. To package product in oxygen is both difficult to control and expensive.

I have now devised an apparatus for the sterilisation or disinfection of packaged articles such as packaged food and drink products.

In accordance with the present invention, there is provided an apparatus for sterilising a packaged product, the apparatus comprising a pair of gas filled electrodes, means for generating a high voltage between the electrodes sufficient to ionise the gas therein and to create a high electromagnetic field therebetween, the apparatus being arranged to irradiate a package containing said product with said field.

Preferably, the electromagnetic field creates cold plasma which is energetic enough to convert oxygen in air into ozone and other reactive oxygen based species. In use, a sealed package containing the product is placed in close proximity to the gas filled electrodes, such that the electromagnetic field generated by the gas filled electrodes penetrates through the wall of the sealed package forming cold plasma from the trapped air inside the sealed package. This cold plasma comprises ozone and other reactive oxygen based species which have a high oxidising potential and kill all micro organisms in contact with the ozone and reactive species resulting in the disinfection of the product as well as the interior of the sealed package.

The present invention efficiently creates ozone and other oxygen reactive species inside a sealed package without any of the above mentioned problems of existing apparatus. Since the apparatus uses gas filled electrodes, there is no electrode erosion and hence has a long life and high reliability. Also, since the gas filled electrodes run cool, there is no need for forced cooling with no degradation of the packaging material. The apparatus is also insensitive to humidity and dust. I have found that nitrous oxide production is also virtually eliminated using this form of ozone production.

Furthermore, the use of plasma creates oxidising species which have a higher oxidising potential than ozone and therefore are more efficient at killing micro-organisms.

Since the invention creates a plasma, it does not involve discharge inside the package therefore there is no harmful discharge through the product. The apparatus is insensitive to package decoration such as labelling or printing and does not deteriorate the decoration. Also, unlike corona discharge this process can be repeated without packaging or product degradation.

Preferably means are provided for directing the generated electromagnetic field towards the product to be sterilised.

Preferably each electrode is elongate and is preferably curved, coiled, bent or otherwise non-linear along its length. Alternatively, each electrode may comprise a plurality of interconnected linear sections.

Preferably each electrode is generally planar, said field directing means being arranged to direct the electromagnetic field perpendicular to said plane towards the product to be sterilised.

Preferably the electrodes generally extend side-by-side along their length and are preferably separated by a substantially uniform gap.

Preferably the electrodes are filled with one or more noble gases such as neon.

Preferably the gas is held under atmospheric pressure or a partial vacuum.

Preferably the gas filled electrodes are made of glass or some other suitable non-conducting material.

Preferably said field directing means extends on one side of the electrodes and comprises a ferromagnetic material. Preferably the material is ferrite or a ferrite composite material which encourages the electromagnetic field to be projected in a single direction. This produces a concentrated electromagnetic field substantially in one direction of the gas filled electrodes. In use, the opposite side of the gas filled electrodes is placed in contact with one of the faces of the sealed package: the electromagnetic field then passes through the wall of the sealed package and thereby maximises the electromagnetic field and hence the cold plasma inside the sealed package.

Preferably said field directing means at least partially extends between the electrodes and preferably comprises a surface which is profiled to received said electrodes. The field directing means has two added benefits: Firstly, it constrains the electromagnetic field in one direction and prevents it from creating unwanted ozone from the air surrounding the gas filled electrodes in all but one direction. Secondly, it prevents any heating effects in closely positioned metal due to electrical induction effects.

Preferably the electrodes are contained within an open-fronted cavity preferably defined by said field directing means. Preferably, the electrodes extend in a plane parallel to the front of the cavity.

Preferably the cavity comprises a side wall or walls which extend around the electrodes and which are arranged to seal against the packaging of the product to be sterilised.

Preferably means are provided for evacuating air or other gas from said cavity when the latter is sealed against the packaging of the product to be sterilised. The suction helps to form a tight seal between the wall(s) of the cavity and the packaging material. The packaging material is thus drawn tight against the open front of the cavity allowing a near air free connection, thereby minimising unwanted generation of ozone in the interface between the gas filled electrodes and the sealed package.

Preferably said high voltage generation means produces voltages pulses in the range of 1 kV to 50 kV.

Preferably said high voltage generation means has a constant voltage component which is of a magnitude sufficient to keeps the gas within the electrodes ionised. This always keeps the gas at the correct gas temperature and eliminates any warm up delays.

Preferably said high voltage generation means produces pulses of high voltage in the range 5 ns to 100 ms duration, so that the current discharge can be controlled.

Preferably said high voltage generation means is arranged to produce pulses of variable magnitude, variable width and/or variable repetition rate, so that the cold plasma formation can be substantially controlled and a wide range of sealed package production rates can be accommodated.

Preferably the apparatus comprises a sensor for monitoring the electromagnetic field, the sensor being connected to means arranged to vary the output parameters of said high voltage generation means. In this way, the high voltage generation means can accept a feedback signal from the electromagnetic field sensor and can automatically adjust the magnitude of the high voltage pulses and the other pulse parameters, in order to adjust the electromagnetic field and maintain it at a constant level. This ensures constant ozone production package to package.

Preferably said high voltage generation means is arranged to produce voltage pulses of opposite polarities and to apply said pulses to respective electrodes. The gas filled electrodes are thus ionised in opposite polarities which significantly improves the efficiency of the ozone generation.

Preferably the apparatus comprises means for agitating or otherwise moving the product to be sterilised: the products may be irradiated with said electromagnetic field before, after and/or during said agitation. Preferably the agitation means is arranged to at least partially rotate the package. This approach encourages the disinfection gas to quickly permeate through the package and get to all surfaces.

Preferably the apparatus is arranged to irradiate successive products. Preferably the apparatus is arranged to successively irradiate the same product.

Also in accordance with the present invention, there is provided an method of sterilising a packaged product, the method comprising placing a package containing said product in proximity to a pair of gas filled electrodes, generating a high voltage between the electrodes sufficient to ionise the gas therein and to create a high electromagnetic field therebetween, and allowing the field to irradiate and penetrate the package so as to create ozone therein.

Preferably a cold plasma field is generated which extends within said package and creates ozone.

Preferably the generated electromagnetic field is directed towards the product to be sterilised.

Preferably the electrodes are contained within an open-fronted cavity, the cavity being sealed against the packaging of the product to be sterilised.

Preferably air or other gas is evacuated from said cavity when the latter is sealed against the packaging of the product to be sterilised.

Preferably the product to be sterilized is moved or agitated before, after and/or during said irradiation.

Embodiments of the present invention will now be described by way of examples only and with reference to the accompanying drawings, in which.

Figure 1:
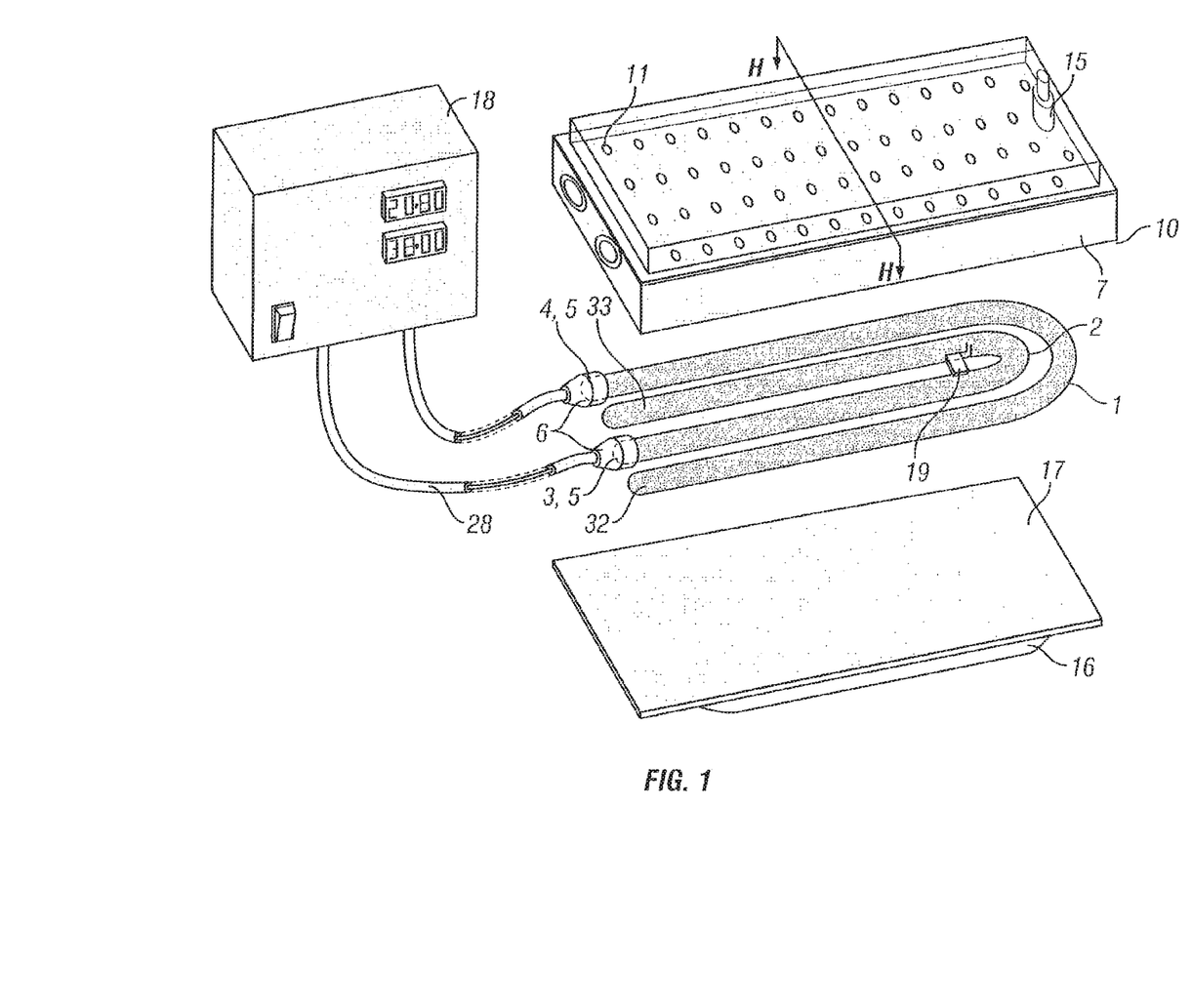
FIG. 1 is an exploded perspective view of a first embodiment of sterilisation apparatus in accordance with the present invention.
Figure 2:
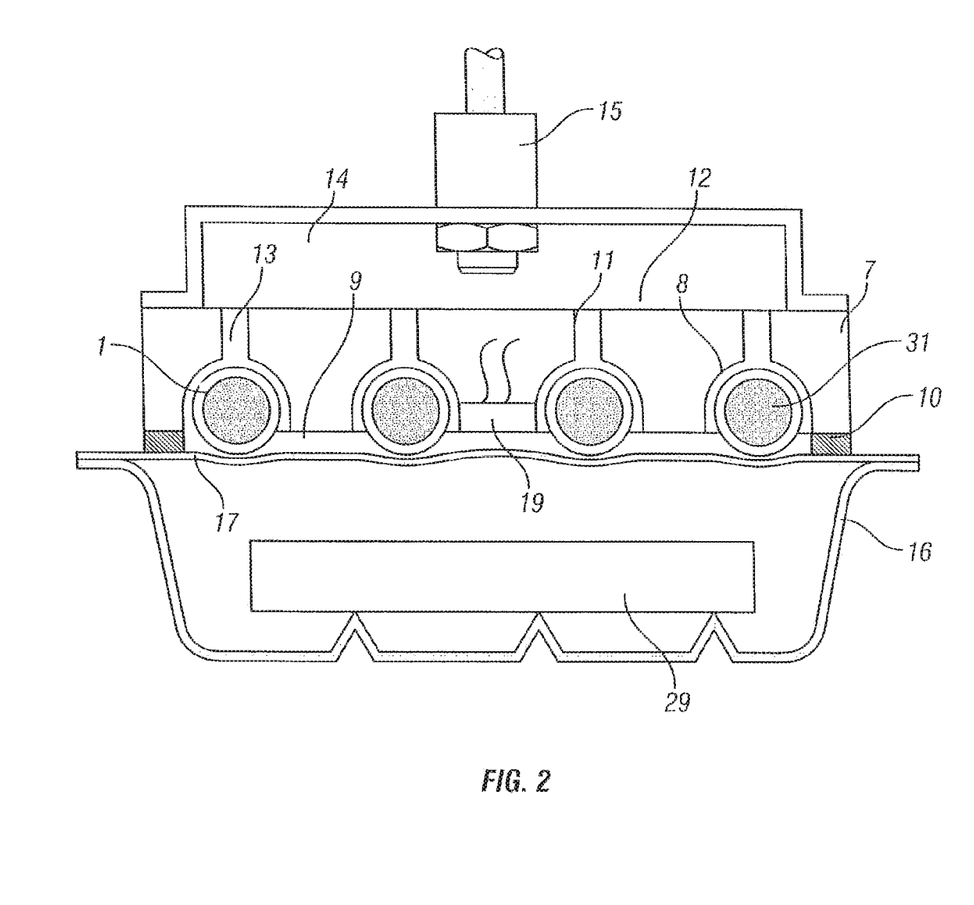
FIG. 2 is a sectional view along the line II-II of FIG. 1.

Referring to FIGS. 1 and 2 of the drawings, there is shown sterilisation apparatus comprising two flat u-shaped electrical discharge tubes 1, 2 formed of a non-conducting material such as glass. The tubes 1, 2 extend side-by-side along their length and are separated by a substantially uniform gap.

The interior 31 of the tubes 1, 2 are filled with a noble gas, such as neon or another ionisable gas under partial vacuum. The tubes 1, 2 are hermetically sealed at both ends 3, 32 and 4, 33. On one end of each tube 1, 2 comprises a metal contact 5, which is covered by an insulator 6 to provide means for connecting a high voltage power supply 18 via wires 28 connected to the metal contacts 5 through the insulators 6.

The discharge tubes 1, 2 are mounted against a reflector 7 which has a front surface, which is profiled to receive the tubes 1, 2. A portion of the reflector 7 extends between each tube. The reflector 7 is made from a ferromagnetic material such as ferrite or a ferrite powder and resin mixture to encourage the electromagnetic field generated by the discharge tubes 1, 2 to project or concentrate substantially forwardly.

The reflector 7 comprises a depending peripheral sidewall provided with a seal 10, which together define a cavity 9 in which the tubes 1, 2 are recessed. The seal 10 is formed of a material which is both flexible and ozone resistant, such as silicone rubber or viton.

A vacuum pump cr other device (not shown) is provided to draw air through the reflector 7 via apertures into a chamber 14 mounted to the rear of the reflector 7. The chamber 14 is connected to the vacuum pump or other device via a duct 15. The wall of the chamber 14 is preferably formed of a non-conducting material such as plastics A sealed package 16 containing the article to be sterilised is positioned in close proximity to front (lower) face of the cavity 9 such that the edges of the package line up with the seal 10. With the sealed package 16 so positioned, suction is applied to duct 15 to produce a tight seal between the sealing film 17 of the sealed package 16 and the to front (lower) face of the cavity 9. The air is substantially removed from the interface between the package 16 and the discharge tubes assembly, which minimises any unwanted ozone outside the package.

A high voltage pulsed dc power supply 18 is provided to ionize the neon gas inside the interior 33 of the discharge tubes 1, 2. The power supply 18 comprises outputs across which the voltage is applied, the outputs being connected to the metal contacts 5 on respective discharge tube 1, 2 via the high voltage wires 28.

Preferably the high voltage dc power supply 18 is arranged to produce pulses of variable magnitude, variable pulse width and variable pulse repetition rate to enable the electromagnetic field strength to be controlled.

The high voltage pulses ionises the neon gas 31 in the discharge tubes 1, 2 which then creates an electromagnetic field to form around and between the discharge tubes 1, 2 and through the sealing film 17 of the sealed package 16. This electromagnetic field is energetic enough to break down the oxygen in the air inside the sealed package 16 to produce cold plasma containing ozone and other highly reactive oxygen species. Any micro-organisms inside the sealed package 16 are killed on contact by the ozone and other disinfecting species in the cold plasma.

Means are provided to automatically control the electromagnetic field strength and hence improve the package to package disinfection consistency by providing a field strength sensor 19 in close proximity to the discharge tubes 1, 2. The sensor 19 converts the field strength measurement to a signal which is fed into the high voltage power supply 18. The high voltage power supply 18 automatically adjusts one or more of its three variables i.e. pulse magnitude, pulse width and pulse repetition rate to maintain constant electromagnetic field strength from the discharge tubes 1, 2. This technique also allows a wide range of packages to be disinfected from one discharge tubes assembly.

The voltage output by the power supply 18 is always sufficient to ionise the gas in the electrodes 1, 2 even when the pulses are not produced: in this manner the electrodes are kept in a state where they can be quickly energised by the pulses to produce the plasma.

Figure 3:
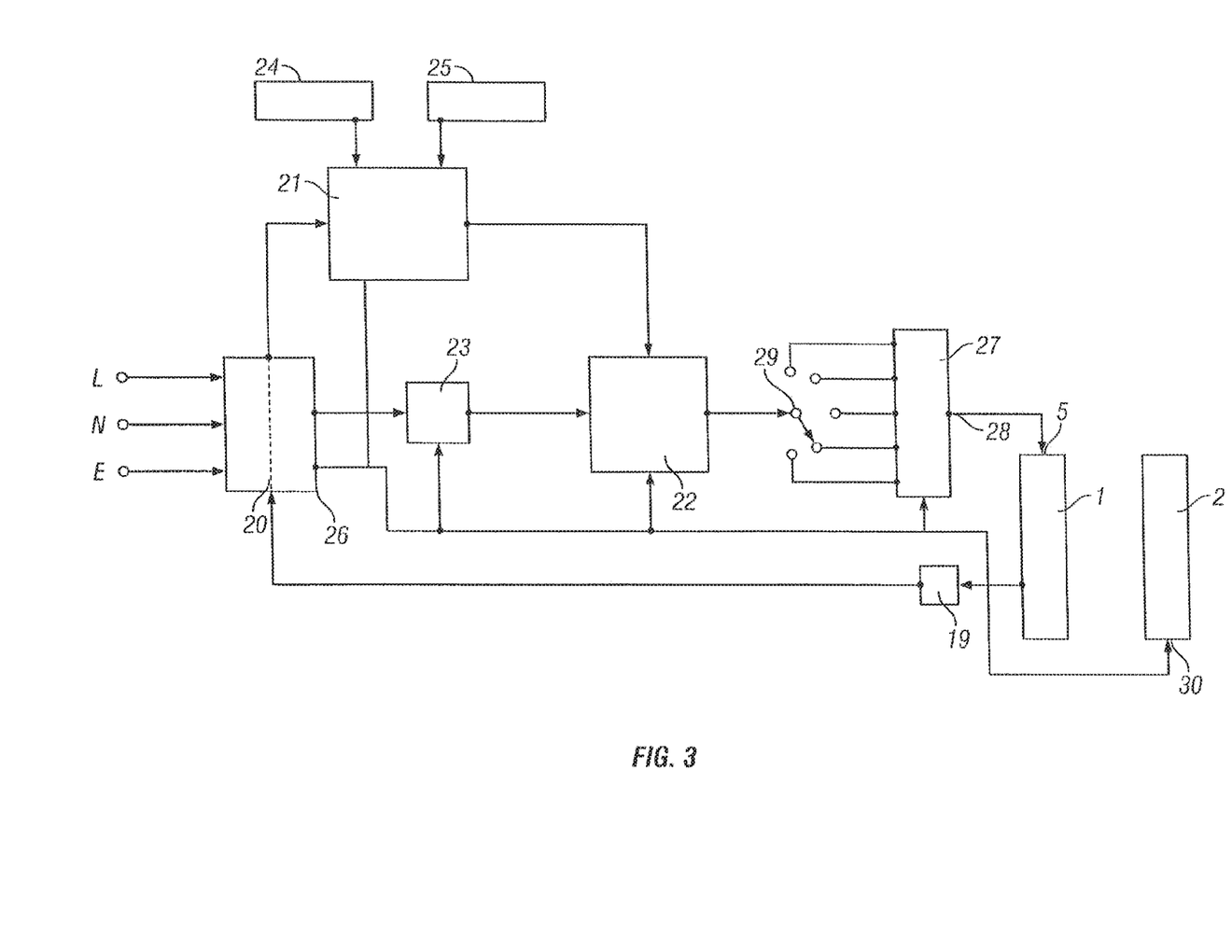
FIG. 3 is a schematic diagram of a power supply circuit of the apparatus of FIG. 1.

Referring to FIG. 3 of the drawings, there is shown a schematic diagram of the high voltage power supply 18 of FIG. 1. The power supply comprises a low voltage dc power supply 20, which has the ability to automatically adjust its dc output from a signal input. The low voltage dc power supply 20 generates a low voltage supply for the pulse generator 21 and the power driver circuit 22 via an EMC filter 23 which removes any high frequency interference. The pulse generator 21 has both variable pulse width control 24 and variable pulse repetition rate control 25 and supplies the drive pulses to switch the power driver device on and off in the power driver circuit 22.

Preferably the power driver device is a power MOSFET device selected to handle the power at the required drive frequency. A transformer 27, whose primary windings are switched by the power driver circuit, steps up the primary voltage to a high voltage at the output 28. Preferably the transformer is designed for high frequency operation and may comprise a high frequency autotransformer.

To enable a selection of high voltages to be generated by the transformer its primary winding is tapped such that the primary to secondary turns ratio and hence the output voltage can be altered and selected by selector 29.

The discharge tubes 1, 2 are connected to the output terminals of the transformer via the metal contacts 5, 30 and the sensor 19, which is in close proximity to the discharge tubes 1, 2, feeds a signal back to the low voltage power supply 20. As the electromagnetic field varies the low voltage power supply 20 uses the signal to automatically adjust the magnitude, pulse width and pulse repetition rate of the low voltage fed to the primary winding of the transformer 27 therefore keeping the electromagnetic field strength substantially constant.

This method can be used with two single discharge tube assemblies positioned on opposite faces of the package or part of the package, so that the electromagnetic field forms between the discharge tubes and through the package from both sides this is an ideal solution for form, fill and seal package processes.

Figure 4:
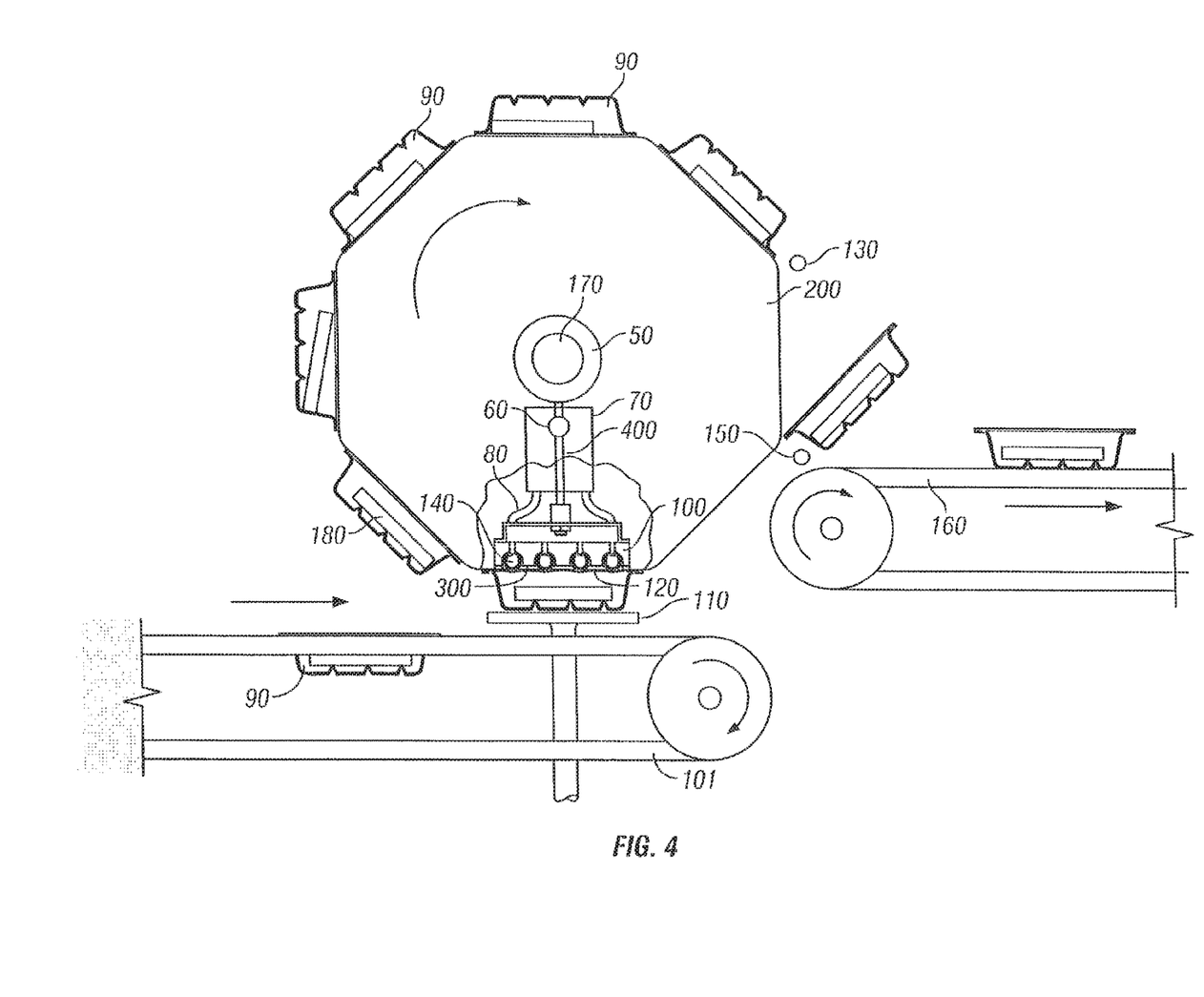
FIG. 4 is a sectional view of a second embodiment of sterilisation apparatus in accordance with the present invention.

Referring to FIG. 4 of the drawings, in the second embodiment apparatus comprises a plurality of discharge tube assemblies 100 as described in the first embodiment, mounted onto a carousel 200. The carousel 200 is octagonal in shape with a eight peripheral faces, each containing one discharge tube assembly 1000 mounted into each of the faces of the carousel 200. Only one assembly 100 is shown in the Figure for clarity. Whilst an octagonal shape is shown for this embodiment the carousel could be many shapes with any number of faces.

Each discharge tube assembly 100 is positioned such that its chamber 300 projects outwardly away from the centre of the carousel 200 and forms the peripheral face of the respective face of the carousel 200. Means (not shown) are provided to make the carousel 200 rotate around a central shaft 170.

Means are provided to pass air through each discharge tube assembly 100 (to form suction at the front face of the chamber 300) in the form of a pipe 400 fixed to the suction chamber 300 on the discharge tube assembly 100 at one end and fixed to a suction manifold 50 at the other end via a valve 60. The valve 60 controls the suction, such that suction is applied when the valve 60 is open and vice-versa. The suction manifold 50 is fixed to a suction source (not shown) via a rotational seal.

Each discharge tube assembly 100 has its own high voltage power supply 70 attached to the carousel 200, which for compactness, are placed alternatively on both sides of the carousel and connected to the respective discharge tube assembly 100 by high voltage wires 80. Means to power the power supplies 70 is provided by a rotating contact assembly (not shown).

The sealed packages 90, requiring disinfection, are fed by an indexing conveyor 101 to the loading position opposite the face of the first discharge tube assembly 100. Means are provided to elevate the package 90 into position on the exit face of the first discharge tubes assembly 100 by a moveable platform 110 and a sensor (not shown) senses that the package 90 is in position.

The sensor energises valve 60 to its open condition and the resultant suction forms a tight seal between the top of the package 90 and the front face of the chamber 300; this also supports the weight of the package 90. The moveable platform 110 withdraws and the carousel 200 indexes by rotation in the clockwise direction to the second discharge tube assembly position. The package 90 is retained by the suction in position tight against the front face of the chamber 300 of the first discharge tube assembly 100 as it indexes around the carousel 200, the first discharge tubes 140 are then switched on to disinfect the package 90 and the sequence repeats.

A sensor 130 senses that a package 90 has reached a discharge position and switches off the discharge tubes 140 and the suction by opening valve 60. The package 90 having no means of support falls forward and is guided onto an exit conveyor 160 by a guide member 150.

As the packages 90 progress around the carousel 200, the product 180 inside each package continually changes posit ion exposing surface area and encouraging the ozone to quickly disperse through the airspace. In this manner, there is a continuous disinfection process for sealed packages 90 and the carousel 200 provides an ample time delay to ensure that sufficient ozone is generated inside the package 90.

Figure 5:
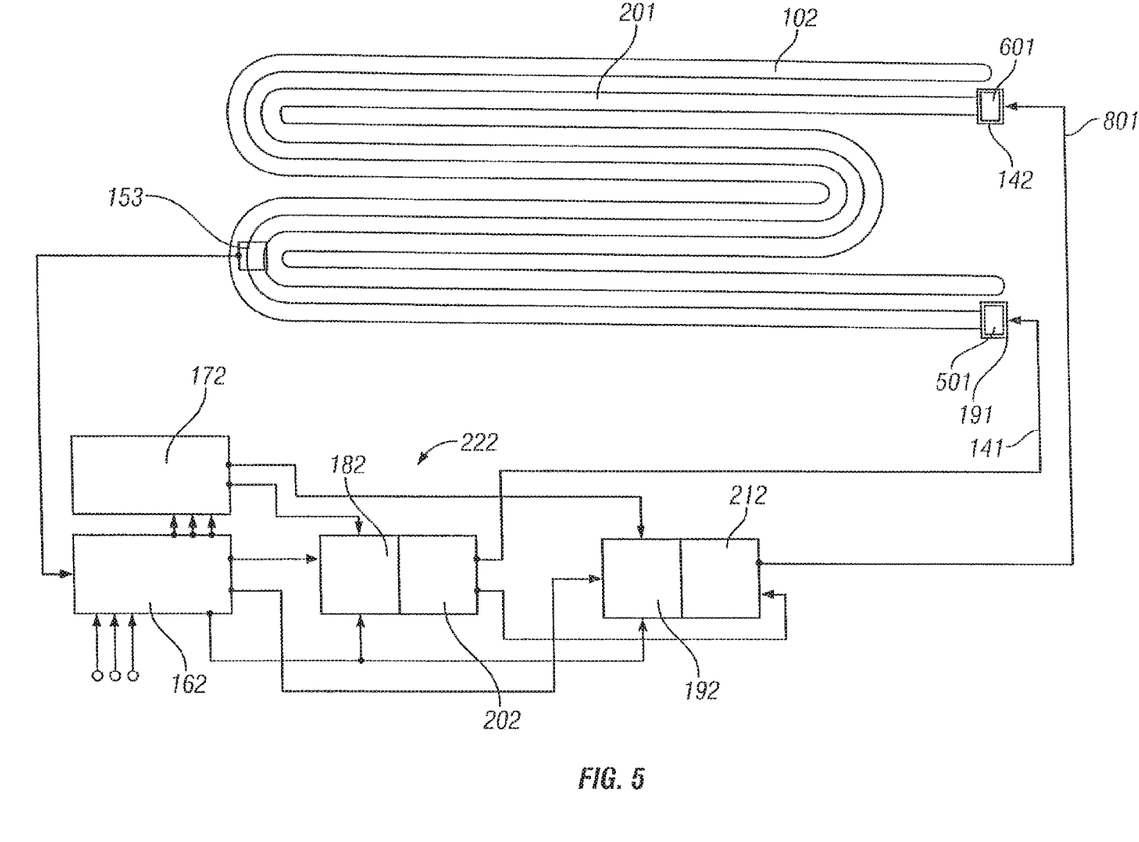
FIG. 5 is a schematic diagram of a third embodiment of sterilisation apparatus in accordance with the present invention.

Referring to FIG. 5 of the drawings, in a third embodiment there is shown a discharge tube apparatus comprising two electrical discharge tubes 102, 201 positioned in close proximity to one another. Each of the discharge tubes 102, 201 are formed of non-conducting material in a tubular form made into a flat serpentine structure comprising of a plurality of parallel tubes which are constructed such that the outlet of the first tube is connected to the inlet of the second tube and so on.

Each discharge tube 102, 201 is filled with a noble gas such as neon or some other ionisable gas under partial vacuum and hermetically sealed at both ends. Means are provided to attach a high voltage power supply 222 to one end of each discharge tube 102, 201 in the form of metal contacts 501, 601.

High voltage wires 801, 141 connected to the metal contacts 501, 601 connect the discharge tubes 102, 201 to the high voltage power supply 222 through suitable high voltage insulators 191, 142. The two discharge tubes 102, 201 are positioned such that the two serpentine forms interleave in a flat plane. Each of the discharge tubes 102, 201 have their own high voltage power supply 182, 202 and 192, 212. The discharge tube 102 is powered from a positive pulsed high voltage with respect to common and discharge tube 201 is powered from a negative pulsed high voltage with respect to common.

The positive and negative high voltage pulses are synchronised to ionise the discharge tubes 102, 201 at the same time. This produces an efficient and very effective of producing cold plasma containing ozone and oxygen species from air.

In some instances to enhance ozone production it is desirable to alternately energise the tubes with positive and negative pulses. The high voltage power comprises a low voltage dc power supply 162 which has the ability to automatically adjust both of its dc outputs from a signal input. The low voltage do power supply 162 generates two low voltage supplies, one positive with respect to common and one negative with respect to common. The positive dc supply feeds the pulse generator 172 and the power driver circuit 182 and the negative dc supply feeds the power driver circuit 192.

To enable the pulse generator 172 to drive both power driver circuits it has complimentary outputs as well as both variable pulse width control and variable pulse repetition rate control. These complimentary drive pulses switch the two power driver devices on and off in the powerdriver circuits 182, 192. Preferably the power driver devices are power MOSFET devices selected to handle the power at the required drive frequency.

Two transformers 202, 212 whose primary windings are switched by the power driver circuits 182, 192 amplify the primary positive and negative voltages to a large positive voltage to drive discharge tube 102 and a large negative voltage to drive discharge tube 201. Preferably both transformers are designed for high frequency operation.

To enable a selection of high voltages to be generated by the transformers 202, 212 their primary windings are tapped, such that the primary to secondary turns ratio and hence the output voltage ranges can be altered and selected.

A field strength sensor 153 which is in close proximity to the discharge tubes 102, 201 feeds a signal back to the low voltage power supply 162. As the electromagnetic field varies the low voltage power supply 162 uses the signal to automatically adjust the magnitude of the voltage fed to the primary windings of the transformers 202, 212 therefore stabilising the electromagnetic field strength.

This present invention is applicable to the disinfection of perishable and non-perishable products in sealed packages across a wide range of applications. The following list is by no means exhaustive and includes food items, bottled drinks, bottled sauces, produce such as salad, medical tools and instruments, baby's bottles etc.

What is claimed is:

1. A method comprising:
    positioning a face of a packet comprising a packaged product adjacent a pair of high voltage electrodes;
    wherein said pair of high voltage electrodes is arranged in a cavity having a cavity face with at least one opening;
    applying a varying voltage to said pair of high voltage electrodes to provide an electromagnetic field through said face of the packet to convert oxygen in air in said packet into ozone and other reactive oxygen based species;
    wherein applying a varying voltage to said pair of high voltage electrodes to convert oxygen in air in said packet into ozone and other reactive oxygen based species does not produce a corona discharge; and
    reducing air pressure in the cavity to draw said packet toward the cavity face of the cavity.

2. The method of claim 1 wherein the packaged product comprises a packaged food product.

3. The method of claim 1 wherein the cavity comprises a side wall or walls which extend around said pair of high voltage electrodes, the method further comprising sealing the packaging of the packaged product against the side wall or walls.

4. The method of claim 1 comprising evacuating air or other gas from said cavity.

5. The method of claim 1 wherein the step of applying a varying voltage comprises providing voltage pulses in the range of 1 kV to 50 kV with a duration in the range of 5 ns to 100 ms.

6. The method of claim 1 further comprising directing the electromagnetic field generated by said pair of high voltage electrodes towards the packaged product.

7. The method of claim 1 wherein said pair of high voltage electrodes is elongate.

8. The method of claim 1 wherein said pair of high voltage electrodes comprises a plurality of interconnected linear sections.

9. The method of claim 1 wherein the electromagnetic field is a high electromagnetic field, and wherein the method further comprises arranging a reflector to direct said high electromagnetic field towards said packet.

10. The method of claim 1 wherein the electromagnetic field is a high electromagnetic field, and wherein the cavity comprises a reflector arranged to direct said high electromagnetic field towards said packet.

11. The method of claim 1 wherein said pair of high voltage electrodes are generally planar, and wherein the step of applying a varying voltage to said pair of high voltage electrodes to provide an electromagnetic field through said face of the packet to convert oxygen in air in said packet into ozone and other reactive oxygen based species comprises directing the electromagnetic field perpendicularly to said face towards said packet.

12. The method of claim 1 wherein said pair of high voltage electrodes generally extends side-by-side along their length.

13. The method of claim 1 wherein high voltage electrodes of said pair of the high voltage electrodes are separated by a substantially uniform gap.

* * * * *